(12) United States Patent
Greenhaff et al.

(10) Patent No.: US 9,662,344 B2
(45) Date of Patent: May 30, 2017

(54) CARNITINE RETENTION

(75) Inventors: Paul Leonard Greenhaff, Beeston (GB); Dumitru Constantin-Teodosiu, Beeston (GB)

(73) Assignees: The University of Nottingham, Nottingham (GB); Lonza Sales LTD., Basel (CH)

( * ) Notice: Subject to any disclaimer, the term of this patent is extended or adjusted under 35 U.S.C. 154(b) by 1223 days.

(21) Appl. No.: 10/549,384

(22) PCT Filed: Mar. 22, 2004

(86) PCT No.: PCT/GB2004/001256
§ 371 (c)(1),
(2), (4) Date: Nov. 3, 2005

(87) PCT Pub. No.: WO2004/082674
PCT Pub. Date: Sep. 30, 2004

(65) Prior Publication Data
US 2006/0240075 A1 Oct. 26, 2006

(30) Foreign Application Priority Data

Mar. 20, 2003 (GB) .................... 0306394.8

(51) Int. Cl.
| | | |
|---|---|---|
| A61K 47/00 | (2006.01) |
| A61K 31/70 | (2006.01) |
| A61K 31/22 | (2006.01) |
| A61K 31/7004 | (2006.01) |
| A61K 31/205 | (2006.01) |
| A61K 45/06 | (2006.01) |
| A23L 33/175 | (2016.01) |

(52) U.S. Cl.
CPC ........ *A61K 31/7004* (2013.01); *A23L 33/175* (2016.08); *A61K 31/205* (2013.01); *A61K 45/06* (2013.01)

(58) Field of Classification Search
USPC ................... 424/439; 514/23, 439
See application file for complete search history.

(56) References Cited

U.S. PATENT DOCUMENTS

| | | | | |
|---|---|---|---|---|
| 4,320,145 A | * | 3/1982 | Cavazza | 514/23 |
| 4,687,782 A | * | 8/1987 | Brantman | 514/561 |
| 4,753,804 A | * | 6/1988 | Iaccheri et al. | 424/491 |
| 5,108,767 A | | 4/1992 | Mulchandani et al. | |
| 5,397,786 A | | 3/1995 | Simone | |
| 5,985,339 A | * | 11/1999 | Kamarei | 426/72 |

FOREIGN PATENT DOCUMENTS

| | | | | |
|---|---|---|---|---|
| EP | 0680945 A2 | * | 2/1995 | C07C 229/22 |
| FR | 2574254 | | 6/1986 | |
| JP | 62198621 | * | 8/1988 | A61K 31/205 |
| WO | WO 86/03380 A1 | | 6/1986 | |
| WO | WO 01/21208 A1 | | 3/2001 | |
| WO | WO 01/82928 A1 | | 11/2001 | |
| WO | WO 01/95915 A1 | * | 12/2001 | A61K 31/70 |

OTHER PUBLICATIONS

Bohles et al, J. Parenteral and Enteral Nutrition, 1984, 8(1), 9-13.*
Gross et al, Biochim. Biophys. Acta., 1993, 1170(3), 265-274.*
van Loon et al, Am. J. Chemical Nutr. 2000, 72, 96-105.*
Boyns et al, British Medical Journal, 1969, 1, 595-598.*
Georges et al, Biochem. Pharmacol. 2000, 59, 1357-63.*
Gross, C.J. et al, "Effect of Development and Nutritional State on the Uptake, Metabolism and Release of Free and Acetyl-L-Carnitine by the Rodent Small Intestine," Biochimica Et Biophysica Acta, Nov. 1993, vol. 1170, No. 3, pp. 265-274.
Bohles H. et al, "Improved N-Retention During L-Carnitine-Supplemented Total Parenteral Nutrition," Jpen. Journal of Parenteral and Enteral Nutrition, Jan.-Feb. 1984. vol. 8, No. 1, Jan. 1984, pp. 9-13.
Greenwood, R.H. et al, "Effects of L-Carnitine on Nitrogen Retention and Blood Metabolites of Growing Steers and Performance of Finishing Steer," Journal of Animal Science, Jan. 2001, vol. 79, No. 1, Jan. 2001, pp. 254-260.
Lacount, D.W. et al, "Responses of Dairy Cows During Early Lactation to Ruminal or Abomasal Administration of L-Carnitine," Journal of Dairy Science, Aug. 1005, vol. 78, No. 8, pp. 1824-1836.
Lacount, D.W. et al, "Dose Response of Dairy Cows to Abomasal Administration of Four Amounts of L-Carnitine," Journal of Dairy Science, Apr. 1996, vol. 79, No. 4, pp. 591-602.
Lacount, D.W. et al, "Ruminal Degradation and Dose Response of Dairy Cows to Dietary L-Carnitine," Journal of Dairy Science, Feb. 1996, vol. 79, No. 2, pp. 260-269.
Ahmed, M., et al., "Postprandial plasma glucose, insulin, glucagon and triglyceride responses to a standard diet in normal subjects." Diabetologia, 1976, 12(1): 61-7.
Beretta-Piccoli, C., P., et al., "Effect of oral glucose loading on plasma insulin, potassium, renin and aldosterone in normal subjects and patients with primary hyperaldosteronism." Clin Exp Hypertens A, 1982, 4(9-10): 1541-58.
Cameron, A. J., et al., "Insulin response to carbohydrate ingestion after gastric surgery with special reference to hypoglycaemia." Gut, 1969, 10(10): 825-30.
Crapo, P. A., et al., "Plasma glucose and insulin responses to orally administered simple and complex carbohydrates." Diabetes, 1976, 25(9): 741-7.
Foss, M. C., et al., "Effect of 50 and 100 g glucose loads on peripheral muscle glucose metabolism in normal man." Diabete Metab., 1992, 18(2): 78-83.
Ganda, O. P., et al., "Metabolic effects of glucose, mannose, galactose, and fructose in man." J Clin Endocrinol Metab., 1979, 49(4): 616-22.

(Continued)

Primary Examiner — Ganapathy Krishnan
(74) Attorney, Agent, or Firm — Kilpatrick Townsend & Stockton LLP

(57) ABSTRACT

A composition for influencing carnitine retention in biological tissue is disclosed. The composition comprises a carnitine substance and an agent to increase sodium potassium ATPase pump activity in the tissue, and/or to increase the activity of a carnitine transport protein, and/or increase blood/plasma insulin concentration.

34 Claims, 10 Drawing Sheets

(56) References Cited

OTHER PUBLICATIONS

Heine, R. J., et al., "The oral glucose tolerance test (OGTT): effect of rate of ingestion of carbohydrate and different carbohydrate preparations." Diabetes Care, 1983, 6(5): 441-5.

Holl, M. G., et al., "Sucrose ingestion, insulin response and mineral metabolism in humans." J Nutr., 1987, 117(7): 1229-33.

Maxwell, J. D., et al., "Plasma insulin response to oral carbohydrate in patients with glucose and lactose malabsorption." Gut, 1970, 11(11): 962-5.

Nuttall, F. Q., et al., "The metabolic response to ingestion of proline with and without glucose." Metabolism, 2004, 53(2): 241-6.

Nuttall, F. Q., et al., "Effect of protein ingestion on the glucose and insulin response to a standardized oral glucose load." Diabetes Care, 1984, 7(5): 465-70.

Parcell, A. C., et al., "Glycemic and insulinemic responses to protein supplements." J Am Diet Assoc., 2004, 104(12): 1800-4.

Schmid, R., et al., "Role of amino acids in stimulation of postprandial insulin, glucagon, and pancreatic polypeptide in humans." Pancreas, 1989, 4(3): 305-14.

Shively, C. A., et al., "Postprandial glucose and insulin responses to various snacks of equivalent carbohydrate content in normal subjects." Am J Clin Nutr., 1986, 43(3): 335-42.

Spiller, G.A., et al., "Effect of protein dose on serum glucose and insulin response to sugars," Am J Clin Nutr., Sep. 1987, 46(3):474-80.

Thibault, L., "Dietary carbohydrates: effects on self-selection, plasma glucose and insulin, and brain indoleaminergic systems in rat." Appetite, 1994, 23(3): 275-86.

Vozzo, R., et al., "Glycemic, hormone, and appetite responses to monosaccharide ingestion in patients with type 2 diabetes." Metabolism, 2000, 51(8): 949-57.

Van Loon, L. J., M. Kruijshoop, et al. (2000). "Ingestion of protein hydrolysate and amino acid-carbohydrate mixtures increases postexercise plasma insulin responses in men." J Nutr 130(10): 2508-13.

Van Loon, L. J., et al., "Plasma insulin responses after ingestion of different amino acid or protein mixtures with carbohydrate." Am J Clin Nutr., 2000, 72(1): 96-105.

Wahlqvist, M. L., et al., "The effect of chain length on glucose absorption and the related metabolic response." Am J Clin Nutr., 1978, 31(11): 1998-2001.

Westphal, S. A., M. C. Gannon, et al. (1990). "Metabolic response to glucose ingested with various amounts of protein." Am J Clin Nutr 52(2): 267-72.

PCT International Search Report and Written Opinion, PCT/GB2004/001256, Jul. 8, 2004, 15 Pages.

Brass, E., et al., "Effect of intravenous L-carnitine on carnitine homeostasis and fuel metabolism during exercise in humans," Clinical Pharmacology & Therapeutics, Jun. 1994, pp. 681-692.

Brass, E., "Supplemental carnitine and exercise[1-3]," The American Journal of Clinical Nutrition, 2000, pp. 618S-23S, vol. 72.

Cederblad, G., et al., "A Method for the Determination of Carnitine in the Picomole Range," Clinica Chimica Acta, 1972, pp. 235-243, vol. 37.

Decombaz, J., et al., "Effect of L-carnitine on submaximal exercise metabolism after depletion of muscle glycogen," Medicine and Science in Sports and Exercise, 1992, pp. 733-740.

Georges, B., et al., "Carnitine Transport into Muscular Cells. Inhibition of Transport and Cell Growth by Mildronate," Biochemical Pharmacology, 2000, vol. 59, pp. 1357-1363.

Greig, C., et al., "The effect of oral supplementation with L-carnitine on maximum and submaximum exercise capacity," European Journal of Applied Physiology and Occupational Physiology, 1987, pp. 457-460, vol. 56.

Harper, P., et al., "Pharmacokinetics of Intravenous and Oral Bolus Doses of L-Carnitine in Healthy Subjects," European Journal of Clinical Pharmacology, 1988, pp. 555-562, vol. 35.

Marconi, C., et al., "Effects of L-carnitine loading on the aerobic and anaerobic performance of endurance athletes," European Journal of Applied Physiology and Occupational Physiology, 1985, pp. 131-135, vol. 54.

Oyono-Enguelle, S., et al., "Prolonged submaximal exercise and L-carnitine in humans," European Journal of Applied Physiology and Occupational Physiology, 1988, pp. 53-61, vol. 58.

Rebouche, C., et al., "Renal adaptation to dietary carnitine in humans [1-3]," American Journal Clinical Nutrition, 1993, vol. 58, pp. 660-665.

Rebouche, C., "Carnitine function and requirements during the life cycle," The FASEB Journal, Dec. 1992, pp. 3379-3386, vol. 6.

Rebouche, C., et al., "Metabolic Fate of Dietary Carnitine in Human Adults: Identification and Quantification of Urinary and Fecal Metabolites," Metabolism and Hormonal Regulation, The Journal of Nutrition, Oct. 13, 2010, pp. 539-546.

Segre, G., et al., "Plasma and Urine Pharmacokinetics of Free and of Short-chain Carnitine after Administration of Carnitine in Man," Drug Research, 1988, pp. 1830-1834, vol. 38, No. 12.

Soop, M., et al., "Influence of carnitine supplementation on muscle substrate and carnitine metabolism during exercise," The American Physiological Society, 1988, pp. 2394-2399.

Stadler, D., et al., "Effect of dietary macronutrient content on carnitine excretion and efficiency of carnitine reabsorption[1-3]", The American Journal of Clinical Nutrition, 1993, vol. 58, pp. 868-872.

Taylor, P., "Absorbing competition for carnitine," Perspectives, Journal of Physiology, 2001, p. 283, vol. 532, No. 2.

Van Loon, L., et al., "The effects of increasing exercise intensity on muscle fuel utilization in humans," Journal of Physiology, 2001, pp. 295-304, vol. 536, No. 1.

Vecchiet, L., et al., "Influence of L-carnitine administration on maximal physical exercise," European Journal of Applied Physiology and Occupational Physiology, 1990, pp. 486-490, vol. 61.

Vukovich, M., et al., "Carnitine supplementation: effect on muscle carnitine and glycogen content during exercise," Medicine and Science in Sports and Exercise, 1994, pp. 1122-1129.

Wyss, V., et al., "Effects of L-carnitine administration in $V_{O2max}$ and the aerobic-anaerobic threshold in normoxia and acute hypoxia," European Journal of Applied Physiology and Occupational Physiology, 1990, pp. 1-6.

European First Examination Report, European Application No. 04722325.0, May 6, 2010, 6 pages.

European Second Examination Report, European Application No. 04722325.0, Apr. 4, 2013, 6 pages.

European Third Examination Report, European Application No. 04722325.0, Jun. 10, 2013, 3 pages.

PCT International Search Report, PCT Application No. PCT/GB2004/001256, Jul. 12, 2004, 6 pages.

Tamir, I. et al., "Effects of a Single Oral Load of Medium-Chain Triglyceride on Serum Lipid and Insulin Levels in Man," Journal of Lipid Research, 1968, pp. 661-666, vol. 9.

"Third Party Observation for Application No. EP 20040722325," Filed by Anonymous, Sep. 18, 2012, 7 pages.

"Third Party Observation for Application No. EP 20040722325," Filed by Anonymous, Apr. 16, 2013, 10 pages.

* cited by examiner

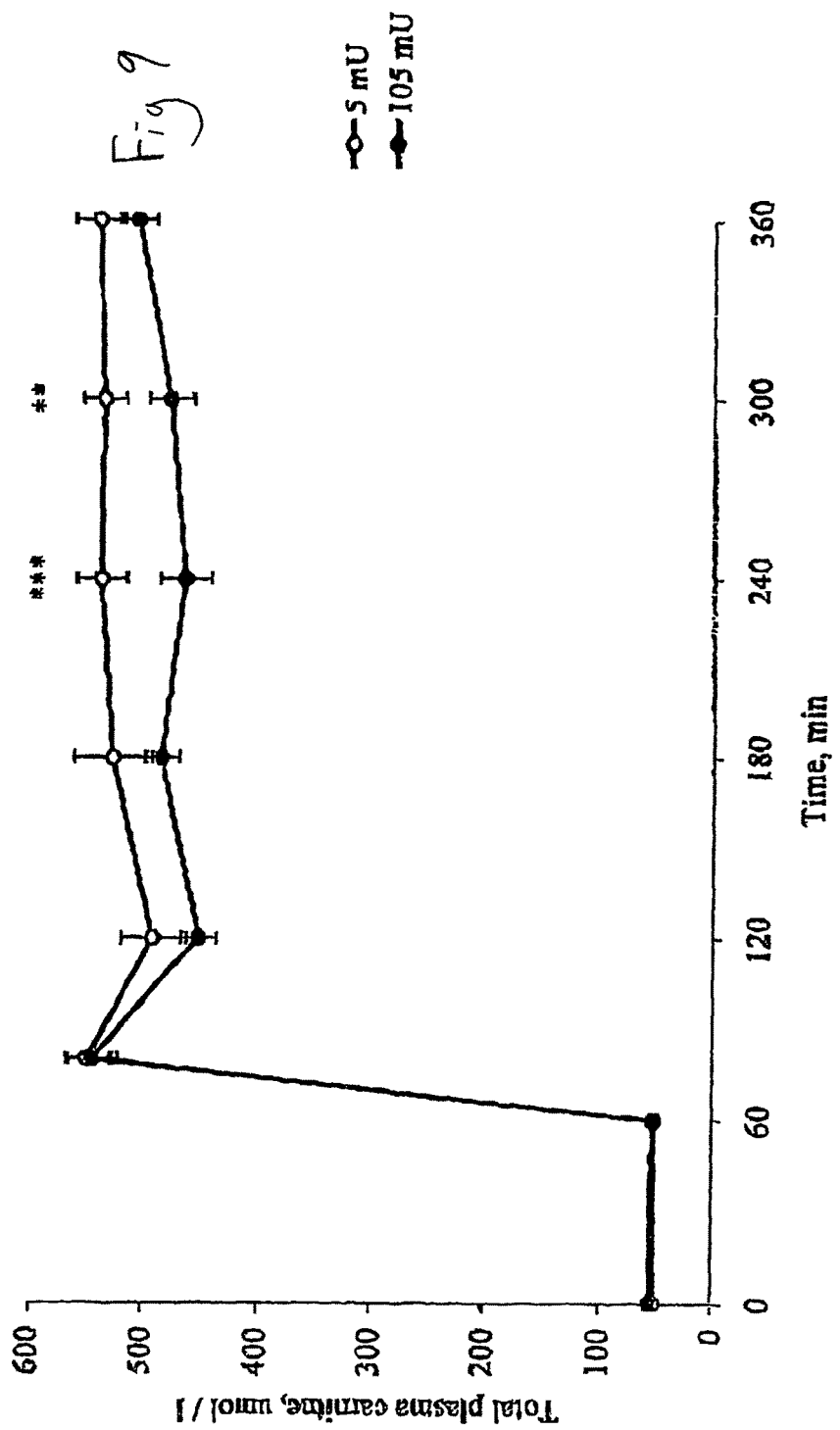

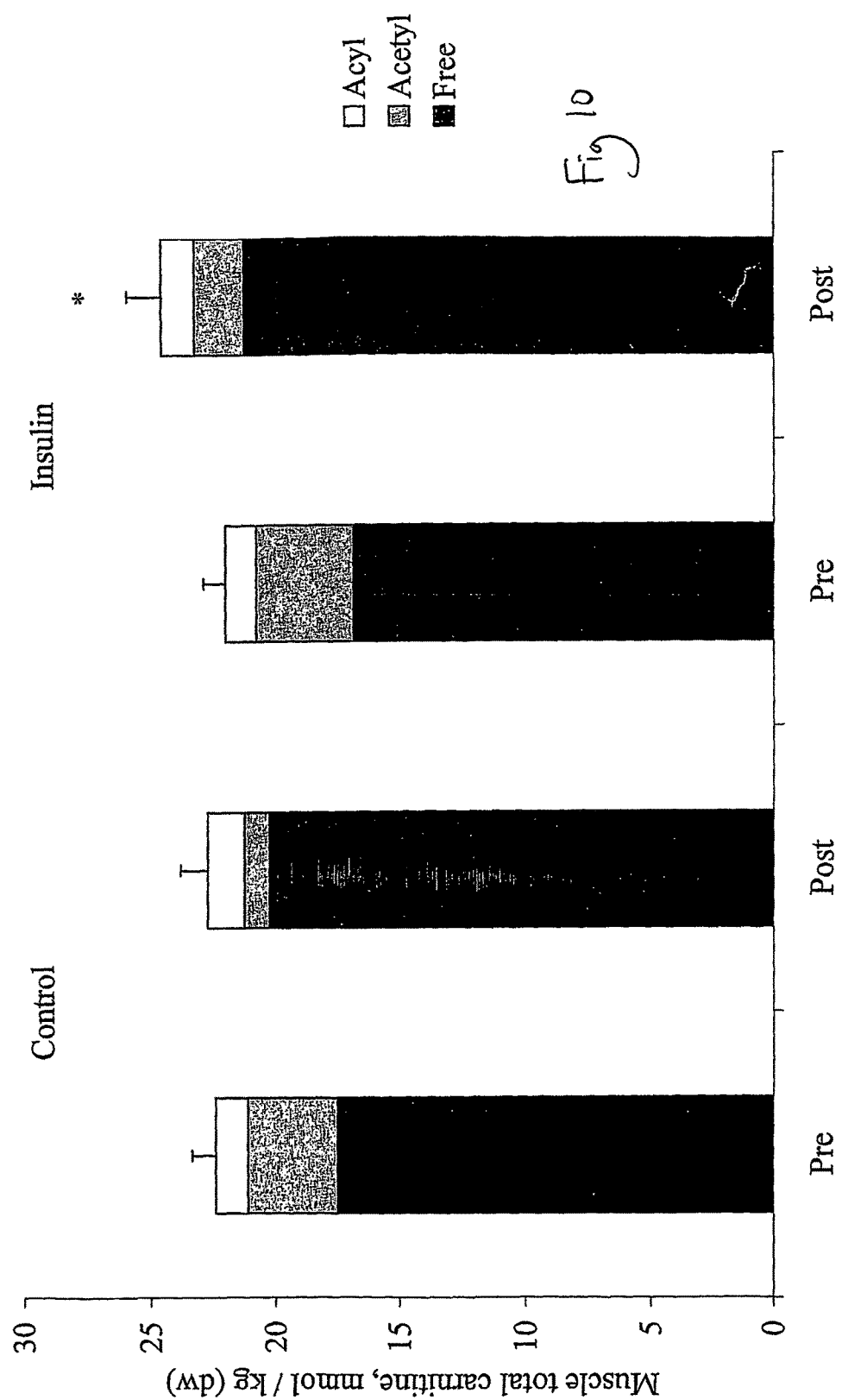

CARNITINE RETENTION

This is a national stage application filed under 35 USC 371 based on International Application No. PCT/GB2004/001256 filed Mar. 22, 2004, and claims priority under 35 USC 119 of United Kingdom Patent Application No. 0306394.8 filed Mar. 20, 2003.

This invention relates to carnitine retention in biological tissue. More particularly, but not exclusively, the invention relates to compositions and methods of increasing carnitine retention in the animal and/or human body.

It is known that carnitine is essential in muscle metabolism and function. In particular the muscle store of carnitine is important for energy production in muscle. If the store of carnitine declines, the function of the muscle can be impaired. Indeed, patients with muscle carnitine deficiency experience premature fatigue and weakness.

Previous studies (Harper et al, 1988, Segre et al 1988, Rebouche 1991), where oral doses of L-carnitine between 2 and 6 g were administered, demonstrate peak plasma concentrations ~3 h after ingestion and state a bioavailability of less than 20%. This poor absorptive status may be due to the fact that intestinal absorption of L-carnitine is normally near saturation (Taylor, 2001). Further studies (Rebouche et al, 1994, Brass et al, 1994) showed that if plasma carnitine concentrations exceed maximum renal reabsorption (60-100 µmol/L), the excess is excreted in the urine with a clearance approximating the glomerular filtration rate. From these features of carnitine's pharmacokinetics, and the fact that the normal plasma carnitine concentration of 40-50 µmol/L is sufficient to yield near maximal rates of skeletal muscle carnitine uptake ($K_M$ 6.4 µM in isolated cells, Georges et al., 2000), it can be predicted that oral L-carnitine supplementation would have little, if any, impact on skeletal muscle carnitine content or metabolism in humans (Brass, 2000).

A study by Vukovich et al (1994) showed that L-carnitine supplementation (6 g every day for up to 2 weeks) resulted in no significant increase in resting skeletal muscle carnitine content and suggested that there was already an adequate amount of carnitine within the muscle to support fatty acid oxidation during exercise. However, Vukovich's study did not look at carnitine status in muscle. The results seen in a study by van Loon et al, 2001 which did look at carnitine status in muscle do suggest, in contradiction to Vukovich, that there is not enough carnitine within the muscle to support fatty acid oxidation during exercise at workloads above 70% maximal oxygen consumption ($VO_2$ max). Other studies (Grieg et al, 1987, Oyono-Enguelle et al, 1988, Soop et al, 1988, Wyss et al, 1990, Decombaz et al, 1993), involved orally supplemented 3-5 g L-carnitine, in subjects with varying levels of fitness, over 5-28 days and measured the effects on various endpoints of exercise. Findings from these studies concluded that there was no effect of L-carnitine on $VO_2$ max, RQ, maximal exercise, fatty acid utilisation, glucose utilisation, lactate, perceived exertion, or heart rate. However, again these studies did not measure skeletal muscle carnitine content. If skeletal muscle carnitine content did not increase then clearly there would not be an affect on skeletal muscle metabolism and thus, an enhancement in the endpoints measured.

In contrast to these findings, Marconi et al (1985) did observe a slight but significant increase in $VO_2$ max in competitive walkers, after oral supplementation of 4 g L-carnitine every day for 2 weeks, which they concluded was most likely due to an increase in TCA flux as lipid metabolism did not change. Vecchiet et al (1990) also observed an increase in $VO_2$ max. However, only a single dose (2 g, orally) was supplemented an hour before exercise and, due to the features of carnitine's pharmacokinetics, it is highly unlikely the observed effects were a result of an increase in skeletal muscle carnitine, which was not measured.

According to one aspect of the present invention there is provided a composition for influencing carnitine retention in biological tissue, the composition comprising a carnitine substance and an agent to increase sodium-potassium ATPase pump activity in the tissue.

The invention further provides a composition for influencing carnitine transport into biological tissue, the composition comprising a carnitine substance to increase blood/plasma carnitine concentration and an agent to increase the activity of a carnitine transport protein.

According to a further aspect of the present invention there is provided a composition for increasing carnitine retention in the animal and/or human body, the composition comprising a carnitine substance and an agent to increase blood/plasma insulin concentration.

The invention also provides a method of influencing carnitine retention in biological tissue, in particular tissue of the animal and/or human body, the method comprising administering to the tissue a carnitine substance and an agent operable to increase sodium-potassium ATPase pump activity in the tissue.

The invention further provides a method of increasing carnitine retention in the animal and/or human body, the method comprising administering to the body a carnitine substance and an agent to increase blood/plasma insulin concentration.

The invention still further provides a method of influencing carnitine transport into biological tissue, the method comprising administering to the body a carnitine substance to increase blood/plasma carnitine concentration and an agent to increase the activity of a carnitine transport protein.

Preferably the method increases carnitine retention in the tissue by increasing the transportation of the carnitine substance, or a derivative thereof into tissue cells. Preferably transportation is increased by stimulation of a sodium dependent transport protein and substantially simultaneously increasing blood/plasma carnitine concentration.

Preferably the agent is operable to increase sodium dependent carnitine uptake into tissue cells, in particular skeletal muscle, liver and/or kidney cells.

The agent may be operable to increase insulin activity in the tissue, desirably by increasing the amount of insulin in the blood/plasma. The agent may comprise carbohydrate or an active derivative thereof. Alternatively, or in addition, the agent may comprise amino acid and/or protein.

Preferably the method involves oral administration and desirably ingestion of the carnitine substance and agent, desirably but not necessarily simultaneously.

According to a still further aspect of the present invention there is provided a food supplement comprising a carnitine substance and an agent as described in any of the preceding paragraphs.

The invention further provides a composition for use in the manufacture of a medicament for influencing carnitine retention in biological tissue, the composition comprising a carnitine substance and an agent to increase sodium-potassium ATPase pump activity in the tissue.

The invention also provides a composition for use in the manufacture of medicament for influencing carnitine transport into biological tissue, the composition comprising a carnitine substance to increase blood/plasma carnitine concentration and an agent to increase the activity of a carnitine transport protein.

There is also provided a composition for use in the manufacture of a medicament to influence carnitine retention in the animal and/or human body, the composition comprising a carnitine substance and an agent to stimulate insulin release and activity in the body.

The invention also relates to the use of a carnitine substance and an agent as described in any of the preceding paragraphs for influencing carnitine retention in human and/or animal tissue.

Carnitine is also provided for use in a method substantially as described in any of the paragraphs above.

A kit is provided according to this invention comprising a carnitine substance and an agent substantially as described in any of the paragraphs above.

According to another aspect of the present invention, there is provided a carnitine substance for use in administration to the human and/or animal body with an agent as described in any of the paragraphs above.

The carnitine substance comprises one or more of carnitine, a functional equivalent of carnitine, an active derivative of carnitine or carnitine analogue. A preferred embodiment may comprise one or more of L-carnitine, a functional equivalent of L-carnitine, an active derivative of L-carnitine or an analogue thereof.

Preferably the agent is a carbohydrate or a derivative of a carbohydrate. The carbohydrate is preferably a simple carbohydrate, which may be a simple sugar. Conveniently, the carbohydrate comprises glucose, but other sugars can be used, for example sucrose or fructose.

Desirably between 10 and 150 times the amount by weight of carbohydrate is administered to one unit of carnitine substance. Preferably between 10 and 95 times, and more preferably between 10 and 40 times, the amount by weight of carbohydrate is administered to one unit of carnitine substance. Desirably at least 0.25 g of the carnitine substance is administered, preferably with at least 2.5 g of the agent. Conveniently substantially 0.25 g of the carnitine substance is administered desirably with between substantially 2.5 g and 37.5 g of the agent, preferably between substantially 2.5 g and 23.75 g, and more preferably between substantially 2.5 g and 10 g of the agent. Conveniently, substantially 3 g of the carnitine substance is administered, desirably with between substantially 30 g to 450 g of the agent, preferably between substantially 230 g and 285 g, and more preferably between 30 g and 120 g of the agent. Conveniently substantially 0.25 g to 3 g of the carnitine substance is administered, desirably with a total of between substantially 2.5 g to 450 g of the agent, preferably between substantially 2.5 g and 285 g, and more preferably between substantially 2.5 g and 120 g of the agent. The agent may be administered to achieve substantially simultaneous elevation of insulin and carnitine concentrations in the blood/plasma.

The composition may be provided in a solution which may be an aqueous solution.

Embodiments of the invention will now be described by way of example only with reference to the accompanying drawings, in which:—

Figure 6:
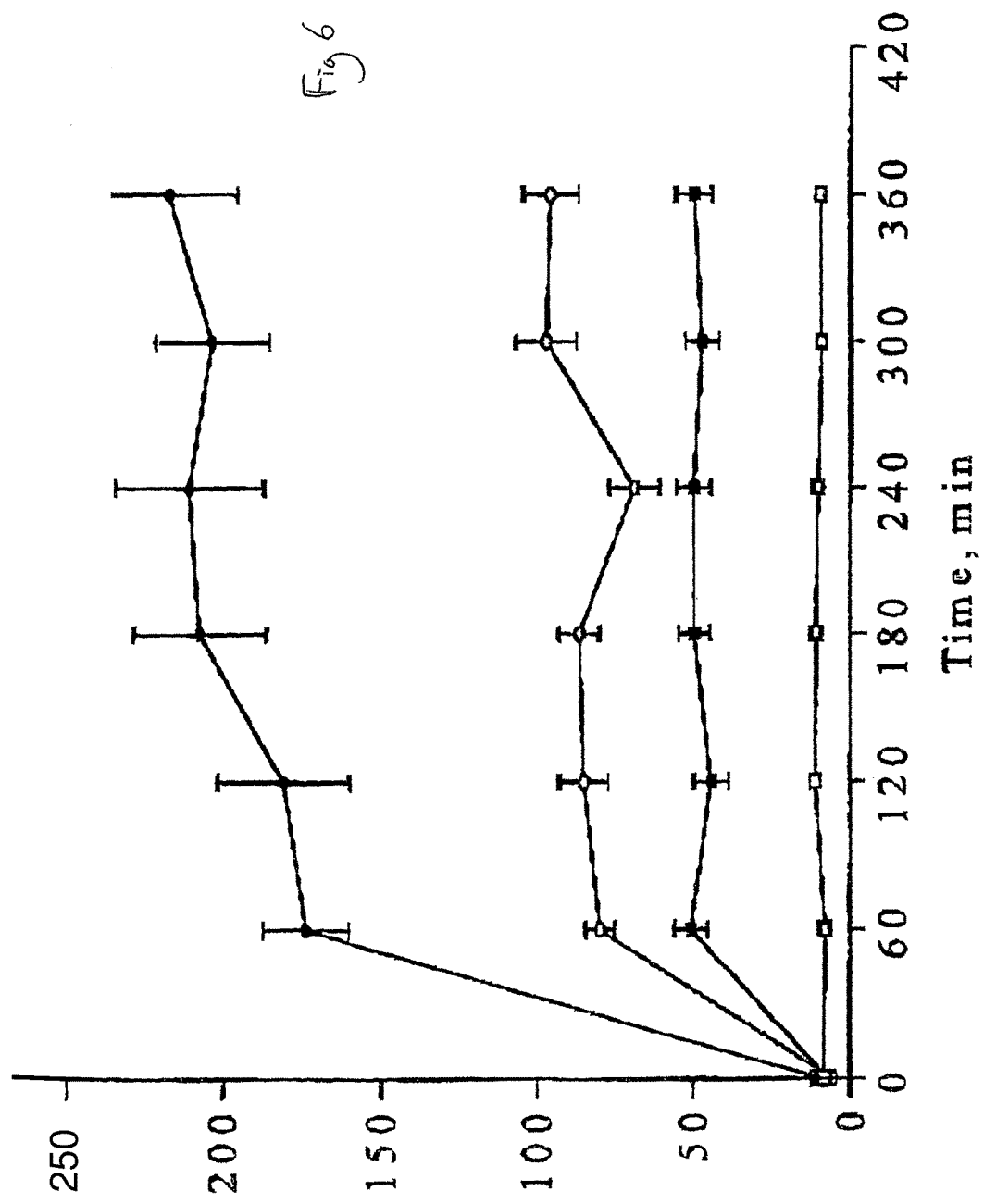
Figure 7:
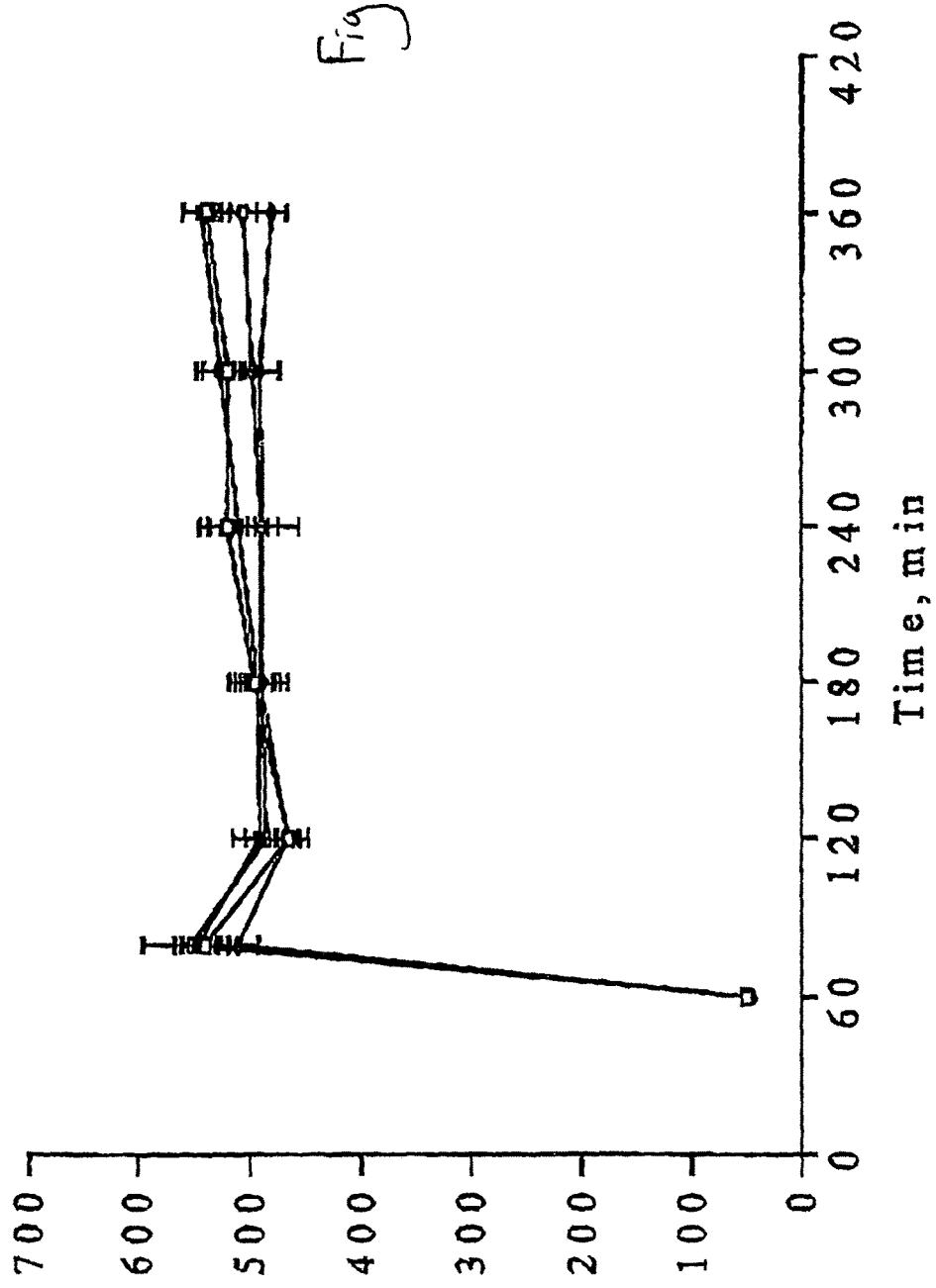
Figure 8:
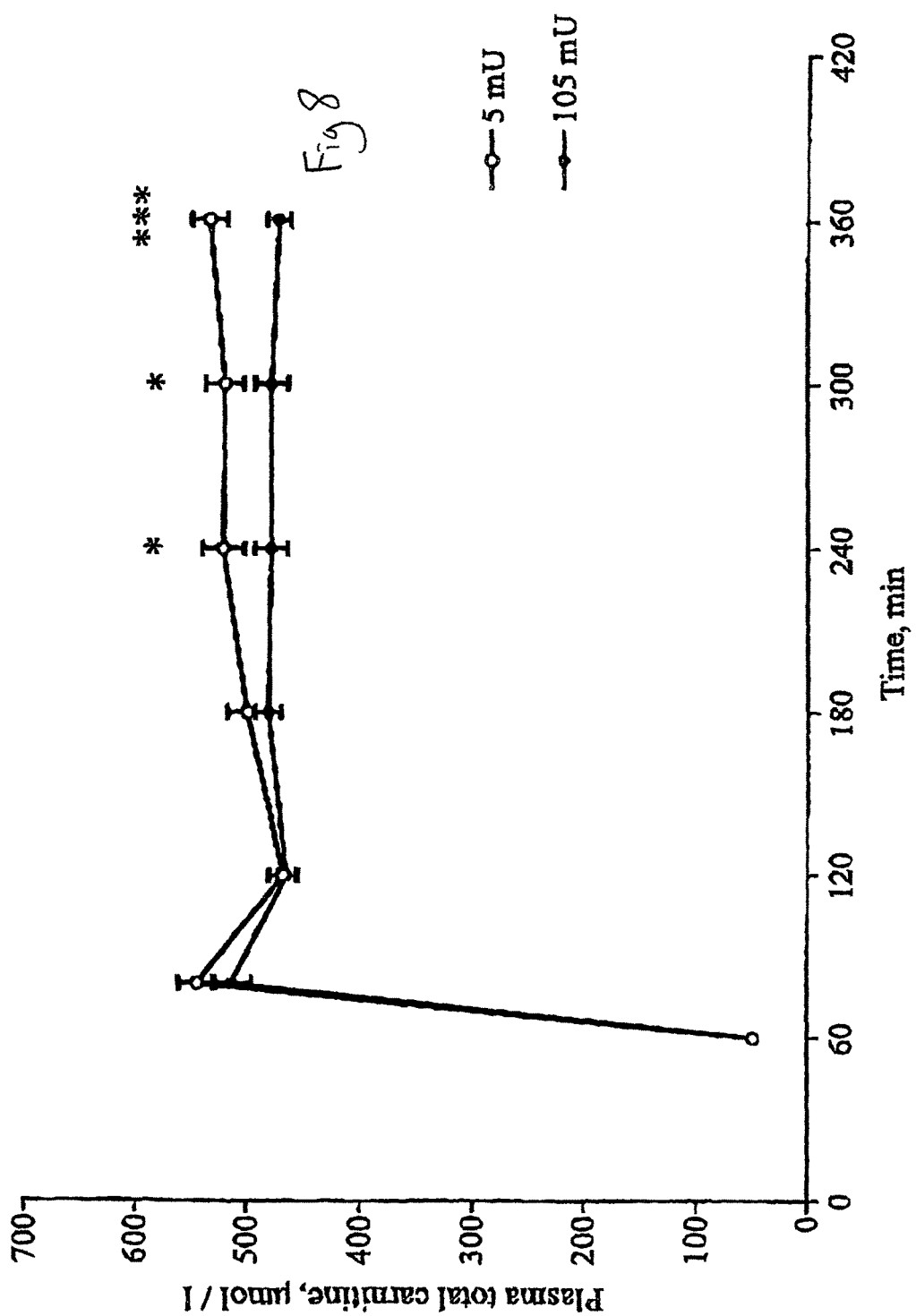

FIG. 6 shows serum insulin concentrations for Example II during 6 hour intravenous insulin infusions of 5 (□), 30 (■), 55 (○) and 105 (●) mU·m$^2$·min$^{-1}$, combined with a 5 hour intravenous 60 mM L-carnitine infusion;

FIG. 7 shows plasma total carnitine concentrations during 6 hour intravenous insulin infusions of 5 (□), 30 (■), 55 (○) and 105 (●) mU·m$^{-2}$·min$^{-1}$;

FIG. 8 shows the plasma carnitine data for Example II for the 5 (○) and 105 (●) mU·m$^{-2}$·min$^{-1}$ doses;

FIG. 9 shows plasma a total carnitine concentration of Example III during 6 hour intravenous infusion of 5 (○) and 105 (●) mU·m$^{-2}$·min$^{1}$ combined with a 5 hour intravenous 60 mM L-carnitine infusion; and FIG. 10 shows muscle acy, acetyl and free carnitine concentrations for Example III pre and post 6 hour intravenous insulin infusions of 5 and 105 mU·m$^{-2}$·min$^{-1}$ combined with a 5 hour intravenous 60 mM L-carnitine infusion.

Referring to the figures, the invention provides a composition, methodology and uses of a composition to influence carnitine retention in tissue such as muscle, liver and kidney tissue in the animal and/or human body which comprise a carnitine substance and an agent to increase blood/plasma insulin concentration with a view to increasing sodium-potassium ATPase pump activity in tissue, and thereby sodium dependent carnitine transport.

The carnitine substance comprises one or more of L-carnitine, a functional equivalent of L-carnitine, an active derivative of L-carnitine or an analogue thereof.

The agent can be anything which acts to increase insulin concentration, including amino acids and protein. However in this embodiment the agent is a carbohydrate such as a sugar, for example glucose which acts to stimulate insulin production in the body.

EXAMPLE I

Eight, healthy, moderately trained, non-vegetarian men (age 22.3±0.7 yr, body mass 79.7±2.5 kg, and body mass index 24.3±0.9 kg/m$^2$) were used in the study of this Example.

The study protocol utilised a blind crossover design where subjects acted as their own controls. Following an overnight fast, subjects reported to the laboratory on two occasions, separated by a 2 week "wash out" period to ensure similar basal muscle carnitine concentrations among experimental treatments. On arrival, subjects voided their bladder and were asked to rest in a supine position on a bed while a cannula was inserted retrogradely into a superficial vein on the dorsal surface of the non-dominant hand. This hand was kept in a hand-warming unit (air temperature 55° C.) to arterialise the venous drainage of the hand and a saline drip was attached to keep the cannula patent.

After a basal blood sample was taken, subjects consumed 3.01 g (3×1.5 g L-carnitine L-tartare effervescent tablets) L-carnitine (Lonza Group, Basel, Switzerland) dissolved in 200 ml of water. After 1 hour and then 3 more times every 1.5 hours (h), subjects consumed a 500 ml drink over a 5 min period in a randomised order containing either sugar free orange drink (Control) or 94 g of simple sugars (CHO) (Original Lucozade, GlaxoSmithKline, Brentford, UK).

Subjects abstained from the consumption of meat, dairy produce, alcohol, and strenuous exercise 24 hours before each visit and for a 24 hour period after the consumption of the carnitine solution. It was essential that subjects had a minimal intake of carnitine in their diet during this period; therefore, food was supplied to the subjects as a ready-made meal, free from carnitine.

During each experimental visit, 5 ml of arterialised venous (a-v) blood were obtained every 20 min for 7 h after which subjects left the laboratory, returning for a final 24 hour blood sample. Two ml of this blood were collected into lithium heparin containers and, after centrifugation (14,000 rpm for 2 min), the plasma was removed and immediately frozen in liquid nitrogen. These samples were then stored at −80° C. and analysed for free and total carnitine concentrations at a later date. The remaining blood was allowed to clot, and, after centrifugation (3,000 rpm for 10 min), the serum was stored frozen at −20° C. Insulin concentration was measured in these samples at a later date with a radioammunoassay kit (Coat-a-Count Insulin, DPC, Ca, USA).

Urine was collected in 5 liter bottles, containing 5 ml of 10% thymol/isopropanol preservative, for 24 h following the consumption of the carnitine drink and returned to the laboratory the following morning where a final blood sample was taken. The 24 h volume was recorded and 5 ml aliquots were removed and stored at −20° C. to be analysed for free and total carnitine concentrations at a later date.

The method used for the determination of carnitine is based on the carnitine acetyltransferase (CAT) catalysed reaction:

L-carnitine+[$^{14}$C]acetyl-CoA ↔ [$^{14}$C]acetyl-L-carnitine+CoASH and measures the concentration of [$^{14}$C]acetyl-L-carnitine. The reaction is reversible, but the removal of COASH via complex with N-ethylmalemide (NEM) ensures the reaction is driven quantitatively to the right and that all the L-carnitine is labelled. To separate labelled acetyl-L-carnitine from any remaining [$^{14}$C]acetyl-CoA Cederblad & Lindstedt (1972) introduced the use of anion-exchange resin. The negatively charged acetyl-CoA remains in the resin whereas the positive acetyl-L-carnitine is excluded for collection.

L-carnitine for use in the standards was purchased from Sigma Chemical Co., St. Louis, Mo. U.S.A., as was the unlabelled acetyl-coenzyme A (sodium salt, purity 90-95%), N-ethylmalemide, and the Dowex 1×8 (200-400 mesh, Cl$^-$ form). [$^{14}$C]acetyl-coenzyme A was obtained from Amersham, Buckinghamshire, UK (specific radioactivity 10 µCi). Carnitine acetyltransferase (5 mg/ml) was obtained from Roche Molecular Biochemicals, East Sussex, U.K. and scintillation liquid (Scintillator Plus) was purchased from Packard Biosciences, Groninger, The Netherlands.

All samples were analysed in duplicate. For plasma samples, 50 µl plasma were pipetted, by positive displacement, into a 3 ml glass test tube. After the addition of 1.2 ml chloroform/methanol ($CHCl_3:CH_3OH$, 3:2) the sample was vortexed, and then centrifuged at 4,500 rpm for 10 min. The supernatant was poured off to another glass tube while the pellet, after being broken up with a plastic rod, was ashed with a further 0.6 ml $CHCl_3:CH_3OH$, vortexed and centrifuged again (4,500 rpm, 10 min). This second supernatant was pooled with the first and the sample was dried by the evaporation of the $CHCl_3:CH_3OH$ under $N_2$.

For total carnitine, all of the acyl-carnitine bonds were hydrolysed by the addition of 100 µl 0.1 M KOH to the test tube. The sample was then placed in a water bath at 50° C. for 2 h. After incubation 20 µl of 0.5 M HCl were added to neutralised the sample.

For free carnitine, 120 µl $H_2O$ (Millipor) were added to make the free and total solutions of equal volume.

For urine samples 10 µl urine were pipetted, by positive displacement, into a 3 ml glass test tube and diluted with 40 µl urine were pipetted, by positive displacement, into a 3 ml glass test tube and diluted with 40 µl $H_2O$ (Millipor). The sample then underwent the same procedure as the plasma sample.

For the preparation of standards, 15, 30, 45, 60, 75, and 90 µl of 40 µmol/l L-carnitine standard solution were pipetted into 3.5 ml test tubes and made up to 120 µl volume by adding $H_2O$ (Millipor). This produced 7 standards with L-carnitine concentrations of 0, 600, 1200, 1800, 2400, 3000, and 3600 pmol/l.

Radioenzymatic analysis of carnitine was carried out by adding twenty-five µl phosphate buffer (1 M, pH 6.5), 25 µl acetyl-CoA (300 µM), 10 µl NEM (40 mM), and 25 µl ($^{14}$C]acetyl-CoA (4 µM) to each tube. Carnitine acetyltransferase (CAT) diluted 1:10 was then defrosted and 20 µl were added to each sample at 20 s intervals. After 30 min incubation at room temperature the contents of each tube were transferred to a column of Dowex 1×8 contained in a Pasteur pipette at 20 s intervals using an automatic pipette (Microlab 1000, Hamilton, Bonaduz, Switzerland). The pipette aspirated each 240 µl sample with a 10 µl air gap, mixed with 250 µl water (Millipor) and then voided the solution into the top of column. The tube was then washed with 250 µl water (Millipor), which were then aspirated, mixed with 250 µl water (Millipor) and voided into the same column. The effluent was collected into 20 ml vials and mixed with 10 ml scintillation fluid. β-radioactivity of each of the vials was counted for 3 min.

A two-way ANOVA (time and treatment effects, SPSS version 10, USA) was performed to detect differences in plasma carnitine and serum insulin. A Student's paired t-test was used to locate differences in 24 h urinary carnitine content and area under plasma time curved between treatments. The total area under the plasma carnitine-time curve was calculated using KaleidaGraph (version 3.51, Synergy Software, USA). Statistical significance was declared at P<0.05, and all the values are means±SE.

The results will now be discussed with particular reference to the drawings.

Figure 1:
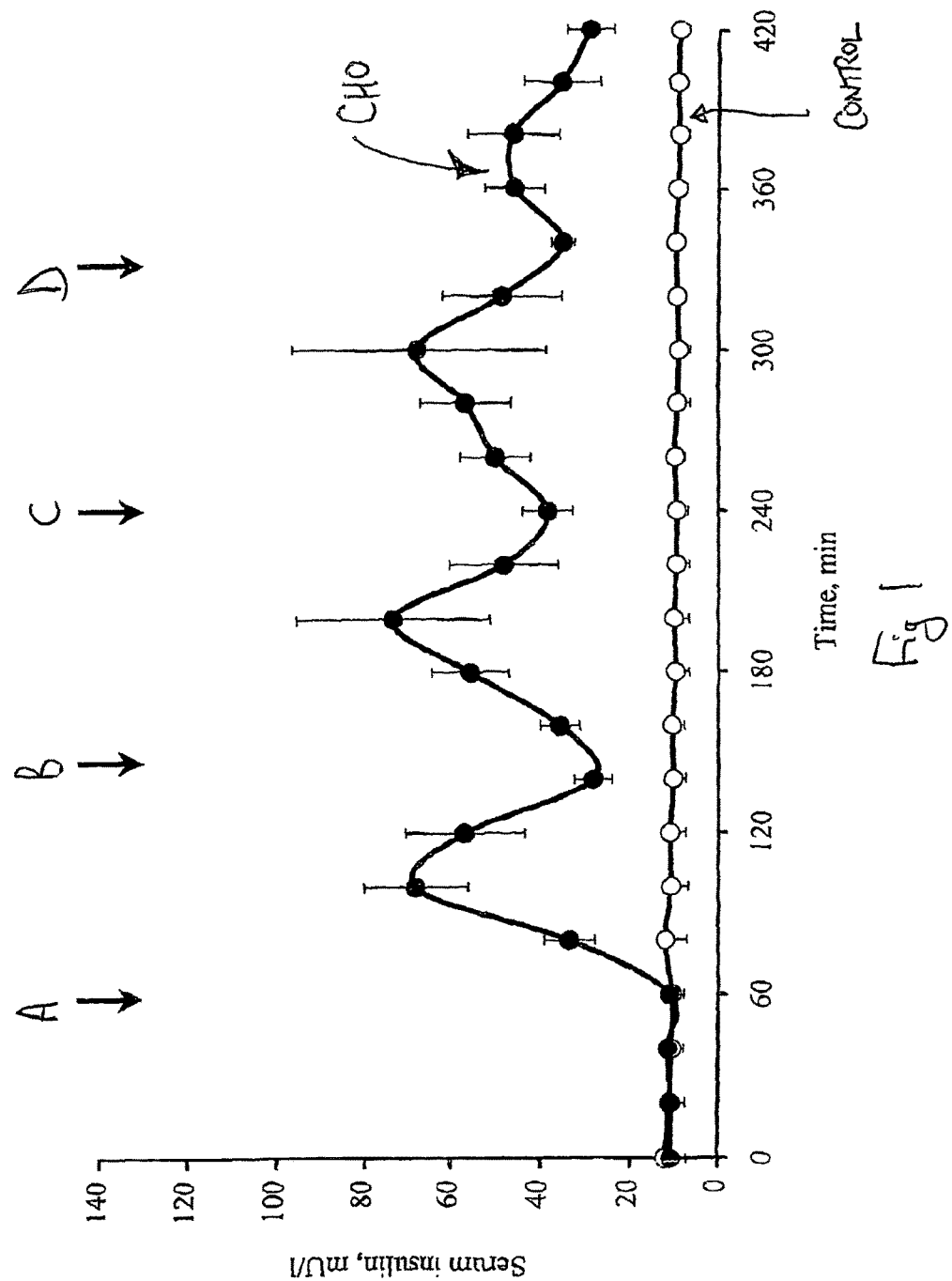
FIG. 1 shows serum insulin concentrations for Example I following carnitine ingestion with Control (○) and CHO (●)

FIG. 1 shows a plot of serum insulin concentrations following carnitine ingestion with Control CON (○) and carbohydrate CHO (●). Insulin concentration was significantly higher (P<0.01) following ingestion of four 500 ml drinks in the carbohydrate group (94 g simple sugars indicated by arrows A, B, C, D at t=60, 150, 240 and 330) than in the control group (sugar free indicated by arrows t=60, 150, 240 and 330). Values are ±SE expressed in mU/l (n=8).

Figure 2:
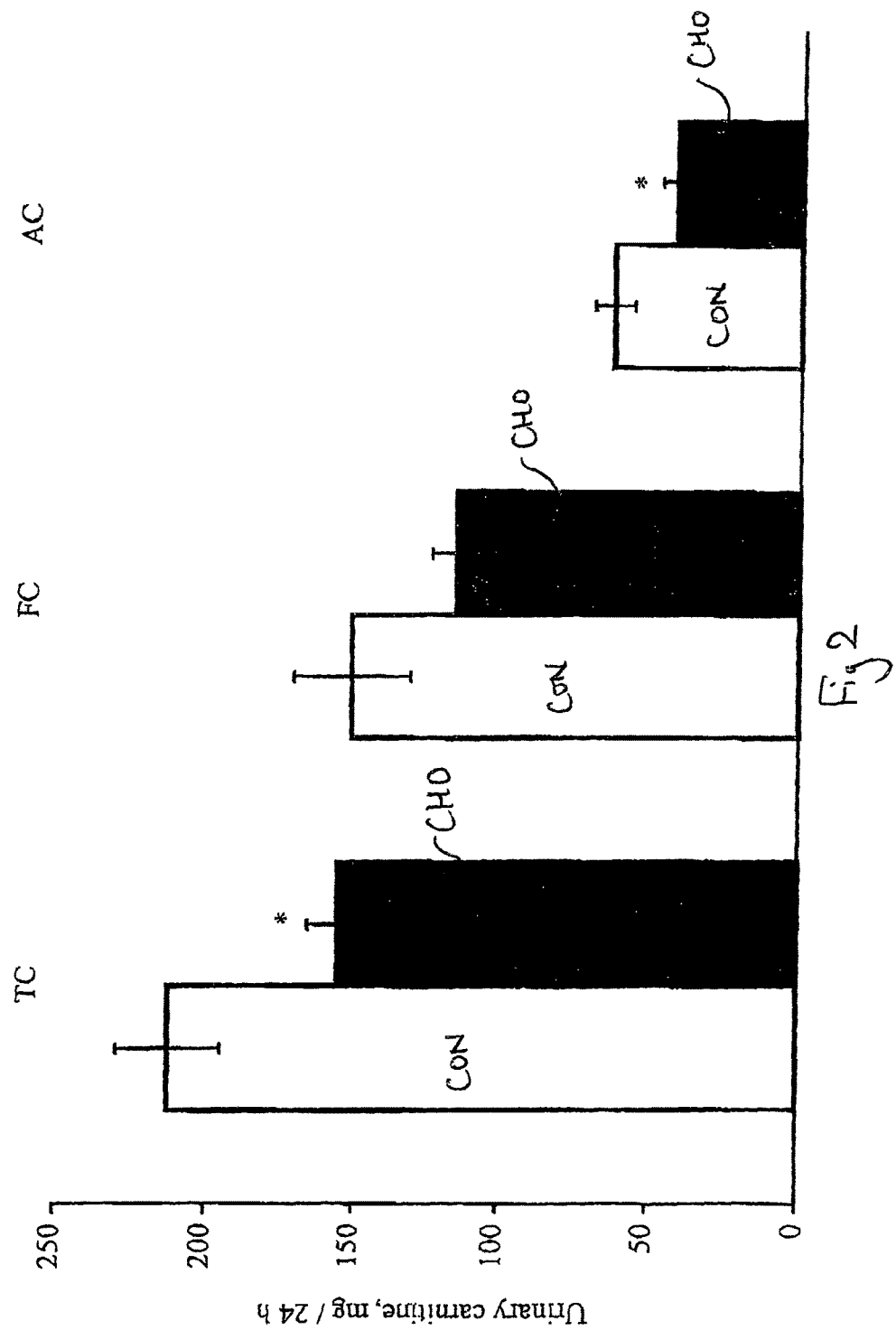
FIG. 2 shows urinary total carnitine (TC), free carnitine (FC) and acylcarnitine (AC) excretion in mg for Example I over 24 hours following carnitine ingestion with Control (□) and CHO (■)

FIG. 2 shows a graph of urinary total carnitine (TC), free carnitine (FC) and acylcarnitine (AC) excretion in mg over a period of 24 hours following an oral dose of 3.01 g of L-carnitine ingestion with control (CON) and carbohydrate (CHO). Mean urinary TC, FC and AC secretion was reduced when subjects consumed CHO compared to Control, and * indicates that excretion was significantly lower in the case of TC and AC (P<0.05). Values are means±SE expressed in mg/24 hr (n=8).

Figure 3:
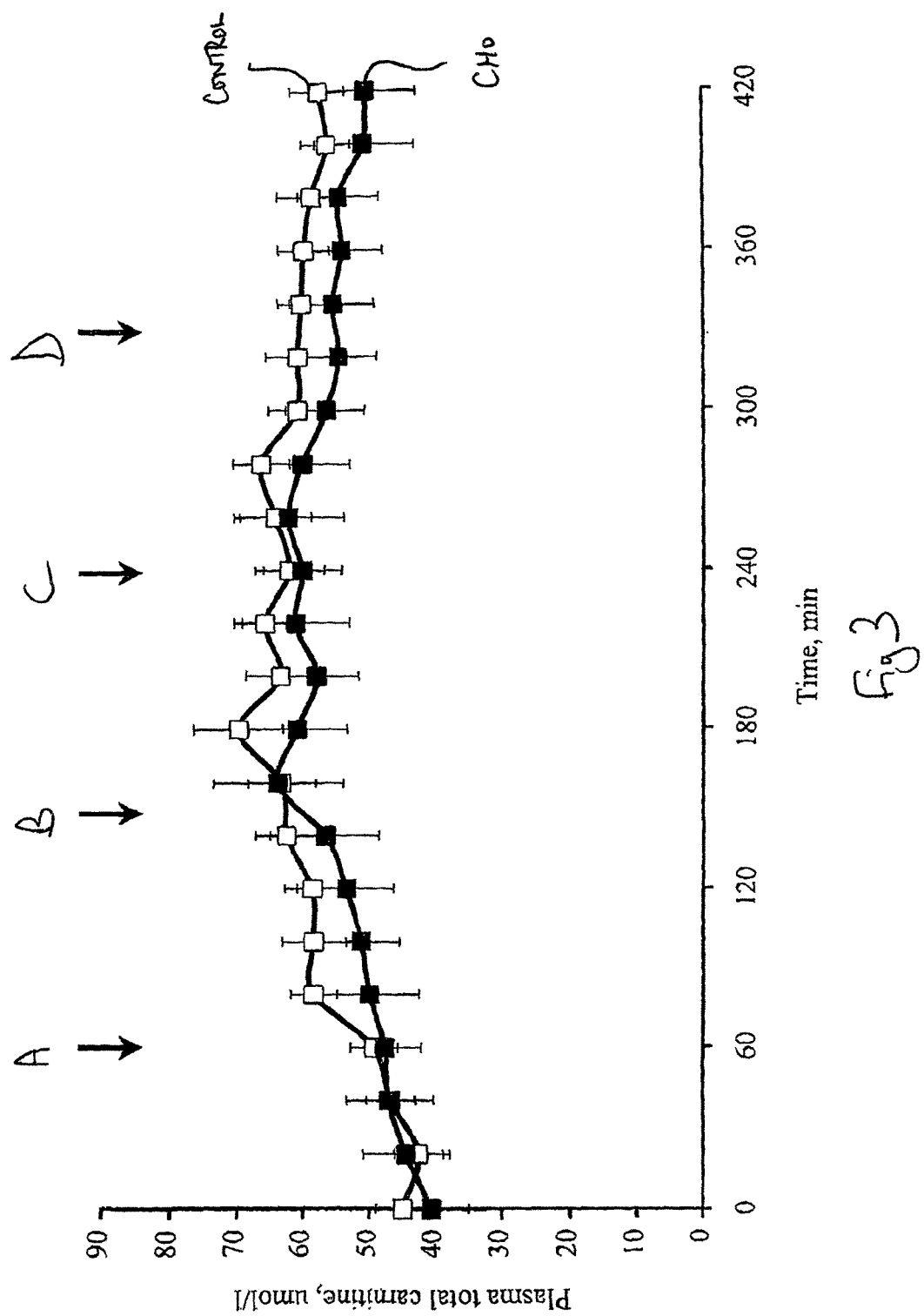
FIG. 3 shows plasma TC concentration for Example I measured over 7 hours following carnitine ingestion with Control (○) and CHO (■). The arrows A, B, C, D indicate time of ingestion of drink.

FIG. 3 shows a plot of plasma total carnitine concentration measured over 7 hours following an oral dose of 3.01 g L-carnitine with Control (□) and carbohydrate (■).

The arrows A, B, C and D indicate time of ingestion of drink. No significant differences (P<0.05) were seen between the two groups (Control and CHO), either at basal or at any point following ingestion. Values are means±SE expressed in μmol/l (n=8).

Figure 4:
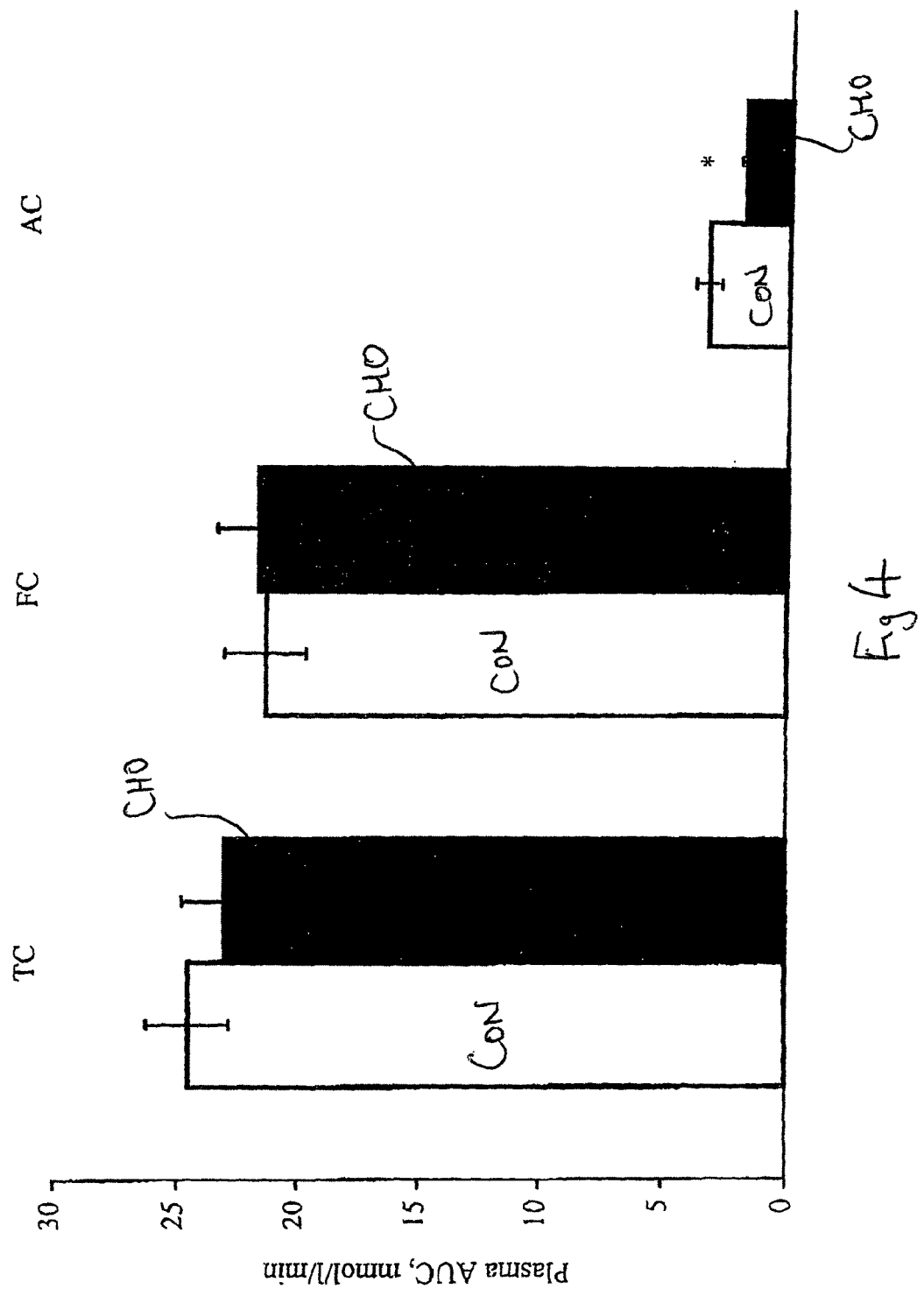
FIG. 4 shows the area under the plasma-time curves (AUC) for Example I for total carnitine (TC), free carnitine (FC) and acylcarnitine (AC) measured over 7 hours following carnitine ingestion with Control (□) and CHO (■).

FIG. 4 shows a plot of the area under the plasma-time curves (AUC) for total carnitine (TC), free carnitine (FC) and acylcarnitine (AC) measured over a 7 hour period following an oral dose of 3.01 g L-carnitine with Control (CON) and carbohydrate (CHO). No significant differences were seen in TC and FC AUC's when comparing Control and carbohydrate, but AC was significantly lower (P<0.05) following CHO, resulting in a significant decrease in plasma carnitine concentration with CHO. Values are means±SE expressed in mmol/l/min (n=8).

The results show that L-carnitine supplementation together with CHO results in a smaller loss of urinary carnitine than that seen with Control. Total (TC), free (FC) and acyl (AC) carnitine were all excreted less with CHO, than in Control.

From the results it can be seen that insulin, released as a result of ingesting carbohydrate (CHO), stimulates L-carnitine retention. Insulin increases carnitine retention most probably by increasing sodium-potassium ATPase pump activity and, thus, sodium dependent transport of carnitine into cells (particularly skeletal and cardiac muscle). Insulin may also enable more FC to be available to tissues by 1) inhibiting acylation of supplemented L-carnitine and/or 2) by stimulating carnitine retention by reabsorption by the kidney.

EXAMPLE II

Seven, healthy, moderately trained, non-vegetarian men (age 20.3±0.4 yr, body mass 76.4±3.1 kg, and body mass index 23.7±1.0 kg/m$^2$) participated in the study of this Example.

The study protocol was as follows.

Subjects reported to the laboratory, following an overnight fast on four occasions, each separated by a ≥2 wk "carnitine wash out" period, having abstained from meat, alcohol and strenuous exercise for the previous 24 h and having voided their bladder immediately prior to entering the laboratory. On arrival, subjects were asked to rest in a semi-supine position on a bed while a cannula was inserted retrogradely in to a superficial vein on the dorsal surface of the non-dominant hand. This hand was kept in a hand-warming unit (air temperature 55° C.) to arterialise the venous drainage of the hand and a saline drip was attached to keep the cannula patent. A second cannula was placed in an antecubital vein in the non-dominant forearm for the infusion of insulin and glucose and a third cannula was inserted into an antecubital vein in the opposite arm for infusion of L-carnitine.

Figure 5:
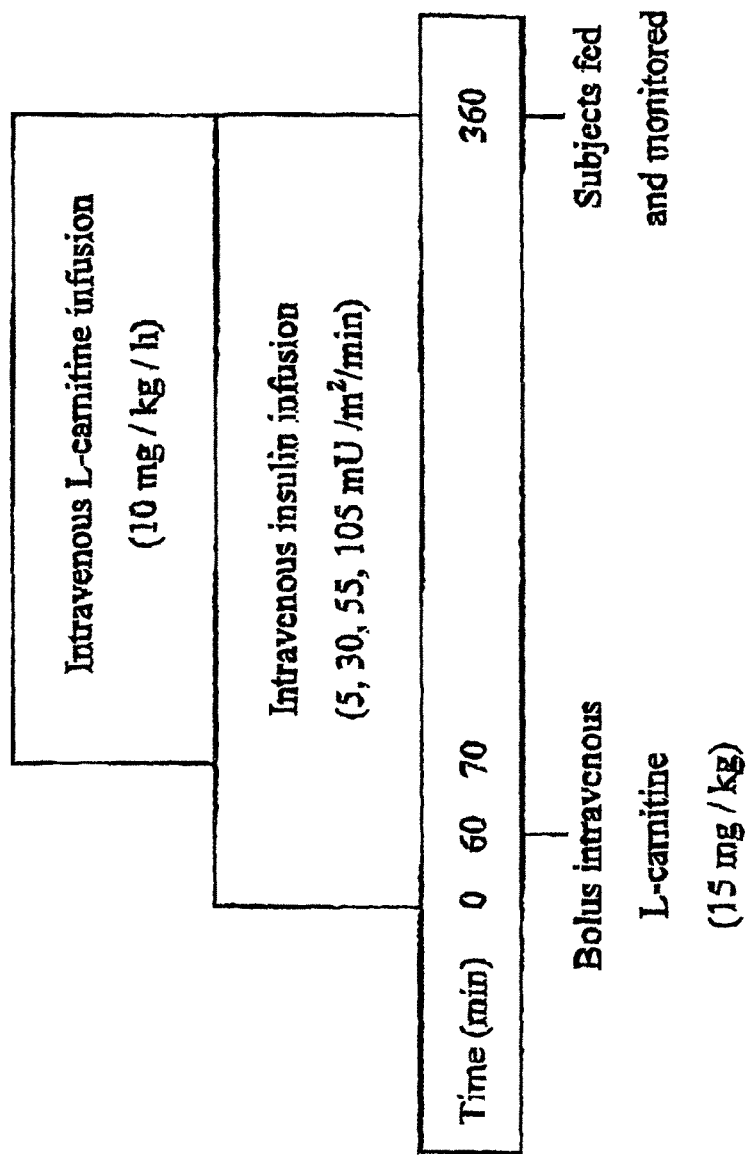
FIG. 5 is a block diagrammatic representation of the study protocol of Example II.

On each experimental visit a 360 min euglycemic insulin (human Actrapid) clamp was performed, whilst maintaining a blood glucose concentration of 4.4±0.01 mmol/l via infusion of a 20% glucose solution. The insulin clamp began at t=0 (FIG. 5) and varied between visits being either 5, 30, 55, or 105 mU·M$^{-2}$·min$^{-1}$ in order to obtain a fasting, fed, physiologically high, or close to supraphysiological serum insulin concentration, respectively. Following a 60 min equilibration period, an intravenous infusion of 60 mM L-carnitine (Lonza Group, Basel, Switzerland) began in conjunction with the insulin clamp, which lasted for the remainder of the protocol (FIG. 5). Specifically, a bolus dose of 15 mg·kg$^{-1}$ L-L-carnitine was administered intravenously over a 10 min period in order to achieve a plasma concentration of ~500 μmol/l. This was followed by a constant infusion at 10 mg·kg$^{-1}$·h$^{-1}$ for the next 290 min to maintain a supraphysiological steady steady state plasma carnitine concentration. At t=360 both insulin and L-carnitine infusions were stopped and subjects were free to leave the laboratory once their blood glucose levels had stabilised.

With reference to FIG. 5 it should be noted that euglycaemia was maintained throughout insulin infusion by means of simultaneous infusion of a 20% glucose solution. During each of the four experimental visits, 1 ml of arterialized venous (a-v) blood was obtained every 5 min to determine blood glucose concentration on-line (YSI 2300 STATplus, YSI, Yellow Springs, Ohio). In addition, 5 ml of a-v blood were obtained every half hour (and at 80 min) for 6 h. Two ml of this blood were collected into lithium heparin containers and, after centrifugation (14,000 rpm for 2 min), the plasma was removed and immediately frozen in liquid nitrogen. These sampled were then stored at −80° C. and analysed for free and total carnitine concentrations at a later date using a radio enzymatic assay. The remaining blood was allowed to clot, and after centrifugation (3,000 rpm for 10 min), the serum was stored frozen at 20° C. Insulin was measured on these sample at a later date using a radioammnassy kit (Coat-a-Count Insulin, DPC, Ca, USA).

A two-way ANOVA (time and treatment effects, GraphPad Prism version 3, GraphPad Software, Inc., USA) was performed to detect differences in plasma carnitine and serum insulin concentrations. If significance was achieved, a repeated measure ANOVA (GraphPad Prism version 3, GraphPad Software, Inc., USA) was used to locate differences between treatments at each time point. Statistical significance was declared at P<0.05, and all values presented represent mean±standard error (SE).

The results will now be discussed with reference to FIGS. 5 to 7 of the drawings.

Following the 60 min equilibration period, steady-state serum, insulin concentration for each of the four insulin infusion protocols (5, 30, 55 and 105 mU·m$^{-2}$·min$^{-1}$) was 10.3±0.3, 47.8±1.3, 85.6±2, 198.6±4.8 mU/l, respectively (FIG. 6). Steady-state serum insulin concentration was markedly different between each of the treatment groups (statistical differences not shown in FIG. 6 for the sake of clarity).

Insulin concentrations during 6 h intravenous insulin infusions of 5 (□), 30 (■), 55 (○), and 105 (●) mU·m$^{-2}$·min$^{-1}$ combined with a 5 h intravenous 60 mM L-carnitine infusion. Values are means±SE expressed in mU/l. Statistical differences not shown in FIG. 6 for the sake of clarity.

Plasma total carnitine (TC) concentration before and throughout the 300 min of 60 mM L-carnitine infusion during each of the four euglycaemic insulin clamps (5, 30, 55, and 105 mU·m$^{-2}$·min$^{-1}$) is shown in FIG. 7. The basal plasma TC concentration was similar across experimental groups, (i.e. 47.7±0.6 μmol/l). The 10 min bolus L-carnitine infusion (15 mg·kg$^{-1}$) markedly increased plasma TC concentration to 545.5±16.4, 546.8±20.7, 559.4±41.2, and 509.7±17.4 μmol/l during each of the insulin clamps (5, 30, 55 and 105 mU·m$^{-2}$·min$^{-1}$, respectively). Plasma TC concentrations fell slightly in each experimental group when the L-carnitine infusion rate was reduced to 10 mg·kg$^{-1}$·h$^{-1}$ (see t=120, FIG. 7), but was thereafter maintained at steady state concentrations well above basal (FIG. 7). Differences in plasma TC concentration between experimental groups became evident during the final 2 h of carnitine infusion. The plasma TC concentration during the 105 mU·m$^{-2}$·min$^{-1}$ insulin infusion was significantly lower than the 5 mU·m$^{-2}$·min$^{-1}$ insulin infusion at t=240 (p<0.05), t=300 (p<0.05), and t=360 (p<0.01; FIG. 3.) Similarly, the plasma TC concentration during 105 mU·m$^{-2}$·min$^{-1}$ insulin infusion was also significantly lower than during the 30 mU·m$^{-2}$·min$^{-1}$ clamp at t=360 (p<0.05).

FIG. 7 shows the plasma total carnitine concentrations during 6 h intravenous insulin infusions of 5 (□), 30 (■), 55 (○), and 105 (●) mU·m$^{-2}$·min$^{-1}$ combined with a 5 h intravenous 60 mM L-carnitine infusion. Values are means±SE expressed in μmol/l.

To highlight the effect of insulin on plasma carnitine concentration, FIG. 8 shows the plasma carnitine data for only the 5 and 105 mU·m$^{-2}$·min$^{-1}$ doses.

As can be seen, plasma carnitine concentration was significantly lower during the final two hours of infusion at the highest dose.

This study maintains a supra-physiological steady state plasma carnitine concentration for 5 h and also combines this with varying steady state serum insulin concentrations.

During 5 h of L-carnitine infusion, plasma total carnitine concentration in a 105 mU·m$^{-2}$·min$^{-1}$ euglycaemic insulin clamp was lower than during a 5 and 30 mU·m$^{-2}$·min$^{-1}$ insulin clamp. This clearly demonstrates that L-carnitine clearance from plasma, either into the urine or periphery, is increased in the presence of high serum insulin levels.

Thus, it would appear that the high serum insulin concentration increased sodium dependent L-carnitine transport into skeletal muscle via activation of the Na$^+$—K$^+$ATPase pump, resulting in the observed fall in plasma total carnitine.

EXAMPLE III

Eight, healthy, moderately trained, non-vegetarian men participated in the present study.

The study protocol was as follows. Subjects reported to the laboratory in the morning after an overnight fast and underwent exactly the same experimental procedures as described in the previous Example II study protocol. However, on this occasion two, as opposed to four, euglycaemic insulin clamps (5 and 105 mU·m$^{-2}$·min$^{-1}$) were performed in a randomised order, and each was separated by 2 weeks. Each clamp was maintained for 6 hours and a muscle biopsy sample was obtained from the quadriceps muscle group in the basal state (prior) to infusion of carnitine and glucose and insulin) and after 6 hrs of infusion. Analytical and statistical procedures were as described above, with the exception of muscle acyl, acetyl and free carnitine carnitine concentrations which were analysed according to the method of Cederblad et al. Statistical differences in muscle carnitine status was determined using Student's Paired T-test.

The results will now be discussed with reference to FIG. 9 of the drawings which shows plasma carnitine concentration during the 5 and 105 mU·m$^{-2}$·min$^{-1}$ insulin clamps. In keeping with the response observed in the previous experiment (FIG. 8), plasma carnitine concentration was significantly lower at the highest insulin infusion does.

FIG. 9 shows the plasma total carnitine concentrations during 6 h intravenous insulin infusions of 5 (○) and 105 (●) 105 mU·m$^{-2}$·min$^{-1}$ combined with a 5 h intravenous 60 mM L-carnitine infusion. Values are means±SE expressed in μmol/1. Statistical differences between treatments:  p<0.01, * P<0.001.

FIG. 10 shows muscle acyl, acetyl and free carnitine concentrations (sum equals muscle total carnitine concentration) pre and post 6 h intravenous insulin infusions of 5 and 105 (●) mU·m$^{-2}$·min$^{-1}$ combined with a 5 h intravenous 60 mM L-carnitine infusion. Values are means±SE expressed in μmol/1. Statistical differences between treatments: * p<0.05.

The lowest insulin infusion rate (equivalent to fasting insulin concentration) had no effect on muscle carnitine accumulation. However, the highest infusion rate resulted in a significant increase in muscle total carnitine concentration.

These findings conclusively demonstrate that:

(i) Carnitine per se does not readily enter the muscle compartment (even when plasma carnitine concentration is dramatically elevated). This observation is in keeping with the notion that carnitine supplementation per se does not elevate the muscle carnitine pool.

(ii) Insulin promotes muscle carnitine accumulation in the presence of elevated plasma carnitine concentrations. This is the first demonstration that insulin can have such an effect. We believe this response is achieved via the stimulatory effect of insulin on sodium dependent muscle carnitine transport. The present invention therefore has useful application in increasing carnitine retention in muscle tissue and thereby reducing the metabolic effects of depleted free carnitine in muscle during exercise, and including the effect on muscle fatigue and muscular performance.

Various modifications may be made without departing from the scope of the present invention. For example other agents may be used which stimulate carnitine retention primarily by way of increasing carnitine transport into tissue, such as insulin or active derivatives thereof. Other agents may include, either as an alternative or as an addition, amino acid(s) and protein(s). Active derivatives, variants or analogues of carnitine may be used. The composition may be administered in any convenient form such as tablet, powder, pellet or the like and otherwise than by ingestion, such as injection.

Between 10 and 150 times the amount by weight of agent such as carbohydrate may be administered to one unit of carnitine substance.

The invention can be used to increase carnitine retention in animal as well as human bodies, and in whole bodies, tissues or cells derived therefrom.

The invention also provides a kit comprising a carnitine substance and an agent such as a carbohydrate, as described above.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A method of increasing carnitine retention in human and/or animal skeletal muscle of a subject, the method comprising orally administering to the subject L-carnitine and an agent to increase blood plasma/serum insulin concentration to greater than 50 mU/L, wherein the amount of L-carnitine is 0.25 g to 3 g and the amount of the agent is 30 g to 450 g.

2. A method for promoting carnitine accumulation in skeletal muscle of a subject in need thereof comprising increasing the serum insulin concentration to greater than 50 mU/L in the subject and orally administering L-carnitine to the subject, wherein the amount of L-carnitine is 0.25 g to 3 g.

3. The method of claim 2, wherein the serum insulin is increased using an agent.

4. The method of claim 3, wherein the agent comprises a carbohydrate.

5. The method of claim 1, wherein the agent is operable to increase sodium dependent carnitine uptake into skeletal muscle.

6. The method of claim 1, wherein the agent is operable to increase insulin activity in skeletal muscle.

7. The method of claim 1, wherein the agent comprises a carbohydrate and/or an amino acid and/or a protein.

8. The method of claim 1, wherein the agent comprises a carbohydrate.

9. The method of claim 1, wherein the agent comprises an amino acid.

10. The method of claim 8, wherein the carbohydrate is a sugar.

11. The method of claim 8, wherein the carbohydrate comprises glucose, sucrose, and/or fructose.

12. The method of claim 1, wherein the amount by weight of the agent is between 10 and 150 times the amount by weight of said L-carnitine.

13. The method of claim 1, wherein the amount by weight of the agent is between 10 and 95 times the amount by weight of said L-carnitine.

14. The method of claim 1, wherein the amount by weight of the agent is between 10 and 40 times the amount by weight of said L-carnitine.

15. The method of claim 1, wherein the amount of L-carnitine is 0.25 g to 3 g and the amount of agent is 30 g to 120 g.

16. The method of claim 1, wherein the amount of L-carnitine is 0.25 g to 3 g and the amount of agent is 230 g to 285 g.

17. The method of claim 1, wherein the L-carnitine and the agent are in the form of a solution.

18. The method of claim 1, wherein the L-carnitine and the agent are in the form of an aqueous solution.

19. The method of claim 3, wherein the agent is operable to increase sodium dependent carnitine uptake into skeletal muscle.

20. The method of claim 3, wherein the agent is operable to increase insulin activity in skeletal muscle.

21. The method of claim 3, wherein the agent comprises a carbohydrate and/or an amino acid and/or a protein.

22. The method of claim 3, wherein the agent is a carbohydrate.

23. The method of claim 3, wherein the agent comprises an amino acid.

24. The method of claim 4, wherein the carbohydrate is a sugar.

25. The method of claim 4, wherein the carbohydrate comprises glucose, sucrose, and/or fructose.

26. The method of claim 3, wherein the amount by weight of the agent is between 10 and 150 times the amount by weight of said L-carnitine.

27. The method of claim 3, wherein the amount by weight of the agent is between 10 and 95 times the amount by weight of said L-carnitine.

28. The method of claim 3, wherein the amount by weight of the agent is between 10 and 40 times the amount by weight of said L-carnitine.

29. The method of claim 3, wherein the amount of agent is 30 g to 120 g.

30. The method of claim 3, wherein the amount of agent is 230 g to 285 g.

31. The method of claim 3, wherein the amount of agent is 30 g to 450 g.

32. The method of claim 2, wherein the L-carnitine is in the form of a solution.

33. The method of claim 2, wherein the L-carnitine is in the form of an aqueous solution.

34. The method of claim 2, wherein the serum insulin concentration in the subject is increased to greater than 50 mU/L and less than or equal to 70 mU/L.

* * * * *